US008551494B2

(12) United States Patent
Shirwan (10) Patent No.: US 8,551,494 B2
(45) Date of Patent: *Oct. 8, 2013

(54) METHODS OF IMMUNE MODULATION WITH DEATH RECEPTOR-INDUCED APOPTOSIS

(75) Inventor: Haval Shirwan, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/897,336

(22) Filed: Oct. 4, 2010

(65) Prior Publication Data
US 2011/0081369 A1   Apr. 7, 2011

Related U.S. Application Data

(60) Division of application No. 10/202,613, filed on Jul. 23, 2002, now Pat. No. 7,927,602, which is a continuation of application No. PCT/US01/02256, filed on Jan. 24, 2001.

(60) Provisional application No. 60/178,038, filed on Jan. 24, 2000, provisional application No. 60/215,580, filed on Jun. 30, 2000.

(51) Int. Cl.
| A61K 39/00 | (2006.01) |
| A61K 38/18 | (2006.01) |
| C07K 14/52 | (2006.01) |
| C07K 14/525 | (2006.01) |

(52) U.S. Cl.
USPC .................... 424/192.1; 424/195.11; 530/350

(58) Field of Classification Search
None
See application file for complete search history.

(56) References Cited

U.S. PATENT DOCUMENTS

| 5,489,528 A | 2/1996 | Kopetzki et al. |
| 5,763,223 A | 6/1998 | Wiley et al. |
| 6,004,942 A | 12/1999 | Firestein et al. |
| 6,042,826 A | 3/2000 | Caligiuri et al. |
| 6,046,310 A | 4/2000 | Queen et al. |
| 6,060,054 A | 5/2000 | Staerz |
| 7,238,360 B2 | 7/2007 | Shirwan |
| 2003/0095977 A1 | 5/2003 | Goshorn et al. |

FOREIGN PATENT DOCUMENTS

| WO | WO 97/18307 | 5/1997 |
| WO | WO 97/33617 | 9/1997 |
| WO | WO 99/17801 | 4/1999 |

OTHER PUBLICATIONS

Pettit D.K., et al. The development of site-specific drug-delivery systems for protein and peptide biopharmaceuticals. Trends in Biotechnology, 1998, vol. 16, p. 343-349.*

Ashkenasy et al., "Display of Fas ligand protein on cardiac vasculature as a novel means of regulating allograft rejection," Circulation, vol. 107, pp. 1-7, 2003.
Pearl-Yafe et al., "Fas ligand enhances hematopoietic cell engraftment through abrogation of alloimmune responses and nonimmunogenic interactions," Stem Cells, vol. 25, pp. 15448-1445, 2007.
Yolcu et al., "Induction of tolerance to cardiac allografts using donor splenocytes engineered to display on their surfaces an exogenous fas ligand protein," Journal of Immunology, vol. 181, pp. 931-939, 2008.
Yolcu et al., "Cell membrane modification for rapid display of proteins as a novel means of immunomodulation: FasL-decorated cells prevent islet graft rejection," Immunity, vol. 17, pp. 795-808, 2002.
Shirwan, "Bone marrow cells engineered with SA-FasL protein establish durable multilineage mixed allogenic chimerism," Unpublished results, discussed in interview of Apr. 12, 2010 for parent U.S. Appl. No. 10/202,613.
Yolcu, "Engineering pancreatic islets with a novel form of FasL protein as a robust means of achieving transplantation tolerance," Unpublished results, discussed in interview of Apr. 12, 2010 for parent U.S. Appl. No. 10/202,613.
Hofmann et al., "Iminobiotin affinity columns and their application to retrieval of streptavidin," Proc. Natl. Acad. Sci. USA, vol. 77, pp. 4666-4668, 1980.
Dubel et al., "Bifunctional and multimeric complexes of streptavidin fused to single chain antibodies (scFv)," J. Immunological Methods, vol. 178, pp. 201-209, 1995.
Airenne et al., "Rapid purification of recombinant proteins fused to chicken avidin," Gene, vol. 167, pp. 63-68, 1995.
Nagata et al., "Fas and fas lignad: lpr and gld mutations," Immunology Today, vol. 16, No. 1, pp. 39-43, 1995.
Daniels et al., "Selective labeling of neurotransmitter transporters at the cell surface," Methods in Enzymology, vol. 296, pp. 307-318, 1998.
Pahler et al., "Characterization and crystallization of core streptavidin," J. Biological Chemistry, vol. 262, No. 29, pp. 13933-13937, 1987.
Chen et al., "Hierarchical Costumulator Thresholds for Distinct Immune Responses: Application of a Novel Two-Step Fc Fusion Protein Transfer Method," the Journal of Immunology, vol. 164, pp. 705-711, 2000.
Darling et al., "In vitro Immune Modulation by Antibodies Coupled to Tumour Cells," Gene Therapy, vol. 4, pp. 1350-1360, 1997.
Sano et al., "A streptavidin-metallothionein chimera that allows specific labeling of biological materials with many different heavy metal ions," Proc. Natl. Acad. Sci., vol. 89, pp. 1534-1538, Mar. 1992.
Notice of Allowance issued on Apr. 29, 2010 by the Examiner in U.S. Appl. No. 10/202,613 (US 2004/0180070).

(Continued)

Primary Examiner — Robert Landsman
Assistant Examiner — Bruce D Hissong
(74) Attorney, Agent, or Firm — Foley & Lardner LLP (57) ABSTRACT

This invention provides chimeric proteins comprising an apoptosis-inducing molecule fused to a member of a binding pair that is capable of binding to a selected cell that expresses a death receptor. When the selected cell is exposed in vivo or ex vivo to the chimeric protein, the selected cell undergoes apoptosis. The preferred embodiment is FasL protein fused to streptavidin. The methods of using the chimeric proteins are especially beneficial in causing activated lymphocytes to undergo apoptosis, thus modulating the immune response. Patients with conditions such as asthma or allergy, or patients undergoing transplantation with allogeneic or xenogeneic tissue are examples of patients who benefit from the methods of this invention.

23 Claims, 10 Drawing Sheets

(56) References Cited

OTHER PUBLICATIONS

Office Action issued on Jun. 23, 2009 by the Examiner in U.S. Appl. No. 10/202,613 (US 2004/0180070).
Office Action issued on Dec. 5, 2008 by the Examiner in U.S. Appl. No. 10/202,613 (US 2004/0180070).
Office Action issued on Feb. 26, 2008 by the Examiner in U.S. Appl. No. 10/202,613 (US 2004/0180070).
Office Action issued on Jun. 4, 2007 by the Examiner in U.S. Appl. No. 10/202,613 (US 2004/0180070).
Office Action issued on Nov. 3, 2006 by the Examiner in U.S. Appl. No. 10/202,613 (US 2004/0180070).
Office Action issued on May 15, 2006 by the Examiner in U.S. Appl. No. 10/202,613 (US 2004/0180070).
Office Action issued on Dec. 2, 2005 by the Examiner in U.S. Appl. No. 10/202,613 (US 2004/0180070).
Office Action issued on Sep. 14, 2005 by the Examiner in U.S. Appl. No. 10/202,613 (US 2004/0180070).
International Search Report issued on Apr. 27, 2001 in application No. PCT/US2002/02256 (corresponding to US 2004/180070).

* cited by examiner

METHODS OF IMMUNE MODULATION WITH DEATH RECEPTOR-INDUCED APOPTOSIS

RELATED APPLICATIONS

This application claims priority to PCT Application Serial No. PCT/US01/02256, filed on Jan. 24, 2001, which claims priority from provisional U.S. Patent Application No. 60/178,038, filed Jan. 24, 2000 and 60/215,580, filed Jun. 30, 2000, all of which applications are incorporated herein by reference.

FIELD OF THE INVENTION

This invention relates to a method to modulate the immune system by the induction of apoptosis in selected cells.

BACKGROUND OF THE INVENTION

The immune system is critical to the survival of vertebrates in an environment full of pathogenic microorganisms. Individuals lacking an immune response through inborn genetic defects, exposure to chemotherapeutic agents or through infection by such viruses as human immunodeficiency virus (HIV), succumb to infections that an individual with a healthy immune system would readily survive. However, the immune system is not always beneficial to the organism. Its dysregulation leads to a variety of pathogenic conditions, including autoimmunity and tumors. The immune system also serves as a barrier for the transplantation of foreign grafts, such as those comprising cells, tissues or organs taken from another individual, a process that can treat a variety of pathogenic disorders, including autoimmunity, replace failed organs in end terminal diseases and treat a variety of hematopoietic disorders via bone marrow transplantation. These applications require either the suppression of the immune system or to "educate" the immune system not to react to self-antigens in the case of autoimmunity and foreign antigens in the case of transplantation.

At the present time, most of the treatment regimens in the fields of autoimmunity and transplantation primarily relay on the suppression of the immune system via the chronic use of variety of immunosuppressive pharmacological agents. Although these drugs are effective in reducing the severity of autoimmune and rejection episodes, they are nonspecific and fail to create a state of permanent antigen-specific tolerance. Their continuous use is therefore required to keep the pathogenic reactions under control. Continuous exposure of the individual to these immunosuppressive agents is, however, associated with a significantly increased risk of opportunistic infections and malignancies. Additionally, these nonspecific immunosuppressive agents can induce serious and undesirable pharmacological side effects in the host. It would, therefore, be very desirable to be able to "teach" the immune system to tolerate selected antigens of interest for the treatment of autoimmunity and induction of transplantation tolerance. The need remains to develop more selective and long-lasting methods to regulate the immune response.

SUMMARY OF THE INVENTION

This invention provides compositions and methods for inducing apoptosis in selected cells. The construction of chimeric proteins comprising apoptosis-inducing protein fused to one of a binding pair capable of binding to the selected cell is taught. The binding pair may be biotin/avidin, biotin/streptavidin, cell surface protein/antibodies to said cell surface proteins or cell surface protein/fragments of such antibodies, such as Fab or HvLv. Preferably the binding pair is biotin/streptavidin. A method is provided wherein effector cells are constructed by exposing said effector cells to biotin, decorating with an effective amount of said chimeric protein and exposing the cells to be killed to said effector cells. The methods to induce apoptosis may be performed in vivo or ex vivo. When the method is ex vivo, it is preferred to attach the chimeric protein to a biotinylated solid matrix. The preferred solid matrix is biotin-agarose beads.

DETAILED DESCRIPTION OF THE INVENTION

An important aspect of immune modulation is to induce tolerance to self antigens and foreign graft antigens for the treatment of autoimmunity and prevention of foreign graft rejection. Both foreign graft rejection and autoimmunity are immunological phenomena primarily initiated by the T cells responding to foreign histocompatibility antigens on the graft and auto-antigens in the host, respectively. This response leads to the activation of cells clonally expressing T-cell receptors (TCRs). Activated T cells then differentiate, proliferate, and synthesize a variety of cytokines, which prolong and intensify the reaction. Experimental animals lacking T cells, either due to congenital immunodeficiency or experimental manipulations, do not develop autoimmunity and accept allografts expressing strong histocompatibility differences for indefinite periods of time. Full T cell activation depends on two distinct signals; signal 1 and 2. Signal 1 is transduced via TCR interaction with the MHC/peptide complex and is antigen specific whereas signal 2 is provided by antigen-presenting cells (APCs) in antigen nonspecific fashion. The transduction of signal 1 in the absence of signal 2 may result in functional silencing (anergy) or physical elimination (apoptosis) of naive T cells. Upon activation, T cells undergo a state of antigen-driven proliferation that allows up to a 1200-fold clonal expansion. A period of death then ensues during which more than 95% of the activated T cells undergo apoptosis (programmed cell death) while the remaining cells differentiate into memory cells as the amount of antigen in the system declines.

Apoptosis plays a central role in both the development and homeostasis of multicellular organisms. Apoptosis can be induced by multiple independent signaling pathways that converge upon a final effector mechanism consisting of multiple interactions between several "death receptors" and their ligands, which belong to the tumor necrosis factor (TNF) receptor/ligand superfamily. The best-characterized death receptors are CD95 ("Fas"), TNFR1 (p55), death receptor 3 (DR3 or Apo3/TRAMO), DR4 and DR5 (apo2-TRAIL-R2). The final effector mechanism of apoptosis is the activation of a series of proteinases designated as caspases. The activation of these caspases results in the cleavage of a series of vital cellular proteins and cell death. In my copending International Patent Application, PCT/US00/34554, filed on Dec. 18, 2000, the teaching of which is incorporated by reference, caspases are disclosed as a useful means to induce apoptosis.

It has now been discovered that Fas-/FasL-induced apoptosis plays a central role in protecting immunologically privileged sites, such as the central nervous system, testes and eyes from immune attack. Allogeneic and xenogeneic tissues transplanted into these sites, for instance, are resistant to rejection. Of great importance is the major role apoptosis plays in maintaining homeostasis in the immune system via activation-induced cell death (AICD). AICD is primarily mediated by apoptotic signals transduced by the Fas/FasL interaction. Fas is a 45 kDa, type I, cell surface protein consisting of a cysteine-rich extracellular domain, which transduce a death signal. Fas mediates effector function by interacting with FasL, a type H membrane protein of about 40 kDa. T cells are the primary cell type in the body that express FasL upon activation. The expression of this molecule makes the activated T cells susceptible to apoptosis. Upon repeated stimulation with antigens, activated T cells up regulate expression of both Fas and FasL on the cell surface and become sensitive to autocrine apoptosis, where Fas engages with FasL expressed on the same cell. Apoptosis may also be induced in a paracrine fashion where Fas of an activated T cell interacts with FasL expressed on another cell. These two modes of apoptotic T cell death control the size of antigen-activated T cell clones and maintain immune homeostasis. All lymphocytes, including B cells, and dendritic cells may be subjected to FasL-regulated immune homeostasis. Dysregulation of AICD is involved in a series of pathophysiological conditions, including degenerative and autoimmune diseases. For example, the autoimmune lymphoproliferative syndrome (ALPS) in humans is an inherited disease of lymphocyte homeostasis and defective apoptosis. In both type I and type II ALPS defects in the Fas receptor or FasL are responsible for the pathogenesis of these diseases. Similarly, congenital mutations causing the lack or low levels of expression of Fas and FasL in the lpr and gld mice, respectively, are associated with severe lymphoproliferative and autoimmune disorders. These mice also lack antigen-induced peripheral clonal deletion of t cells. Transgenic expression of Fas in lpr/lpr mice results in amelioration of autoimmunity and restoration of AICD-induced clonal deletion of T cells, providing direct evidence for the importance of Fas/FasL-mediated apoptosis in peripheral tolerance to self-antigens. The critical role FasL plays in AICD and the importance of AICD in peripheral tolerance form the basis of this patent application to use the death ligands as immunomodulators to induce tolerance both to auto and foreign antigens for the treatment of autoimmunity and prevention of foreign graft rejection.

Figure 1:
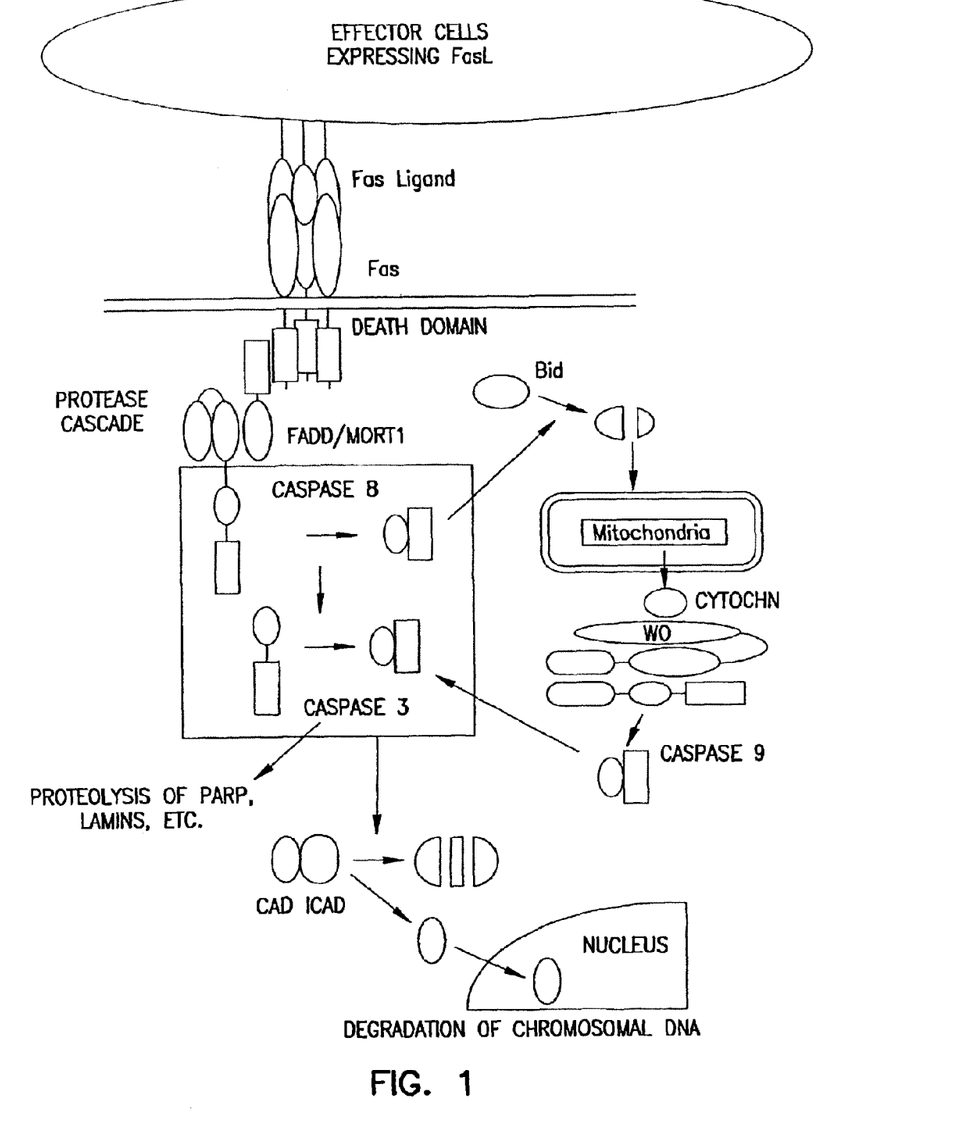
FIG. 1 shows the mechanism of Fas/FasL-induced apoptosis.

The molecular mechanism of death receptors/ligands-induced apoptosis has been elucidated in great details. For example, Fas/FasL-mediated apoptosis is induced by binding of three FasL molecules which induces trimerization of Fas receptor via C-terminus death domains (DDs), which in turn recruit an adapter protein FADD (Fas-associated protein with death domain) and Caspase-8 (FIG. 1). The oligomerization of this trimolecular complex, Fas/FAIDD/caspase-8, results in proteolytic cleavage of proenzyme caspase-8 into active caspase-8 that, in turn, initiates the apoptosis process by activating other downstream caspases through proteolysis, including caspase-3. Death ligands in general are apoptotic when formed into trimers or higher order of structures. As monomers, they may serve as antiapoptotic agents by competing with the trimers for binding to the death receptors.

The present invention discloses how to generate death ligands consisting of stable tetramers and deliver these ligands either as purified proteins or exposed on the surface of APCs to induce apoptosis in lymphocytes expressing the counter death receptors. We hypothesize that death ligands are more effective in inducing apoptosis when in trimers or higher order of structures based upon the available data from similar biological systems. The preferred embodiment for the formation of tetramers and higher order of structures is streptavidin or avidin, both of which form tetramers and higher structure under physiological conditions. A modified form of streptavidin has been chosen as the preferred molecule in this patent application and is referred to as CSA throughout this document.

Apoptosis of activated T cells results in tolerance to allografts and xenografis, including bone marrow and other organ transplantation. Purging of activated T cells also relieves the symptoms of allergies and other immune-induced diseases. Included in the latter are autoimmune disorders such as multiple sclerosis, lupus erythematosus, sarcoidosis, diabetes, and rheumatoid arthritis. Many disorders, including some tumors, are dependent on lymphocyte functions that lead to persistence of the disorder. Many hematological disorders could be treated with bone marrow stem cell transplants if the immune response could be regulated so as to induce tolerance to the foreign stem cells. Among these disorders are leukemias, lymphomas, aplastic anemia, sickle cell and Cooley's anemia and the like. All of these disorders may be controlled permanently or temporarily by apoptosis of activated immune cells, including T cells.

This invention discloses strategies for the induction of tolerance, which comprise the construction of chimeric cDNAs encoding the functional portions of a tetramer forming molecule operably linked to an apoptosis-inducing molecule. Table I is a summary of the proposed constructs. Choice of constructs may be based on factors such as the nature of the foreign antigen provoking adaptive immunity; whether relief sought will be temporary or permanent; whether a commitment to death is desired or addition downstream regulation of apoptosis is preferred. It is to be understood that the constructs listed are representative of the invention only and are not limitations. Those skilled in the art can readily, without undue experimentation, make constructs with any of the death ligands, FasL, TNFα, TRAIL (Apo2 ligand), and TWEAK (Apo3 ligand) or the like, operably linked to a tetramer-forming molecule. Those skilled in the art are aware that many pharmaceutical agents enhance apoptosis. Among such agents are bis-indolylmaleimide-8 and quabain. If desired, these agents may be used in conjunction with the chimeric proteins of this invention.

TABLE I

| Construct | Insert | Made | Function | Application |
|---|---|---|---|---|
| rsFasL | Soluble extracellular portion of rat FasL | + | Anti-apoptotic | Treatment of neuro-degenerative disorders and promotion of liver regeneration |
| mFasL | Rat FasL modified to be stably expressed on the cell surface | + | Apoptosis | Tolerance to allografts, xenografts, bone marrow transplantation, treatment of autoimmune diseases, allergies, asthma, septic shock, and other immune-induced diseases, and lymphocyte-dependent disorders, including tumors and promotion of liver regeneration |
| wtFasL | Rat wild type molecule | | Chemotactic, Anti-apoptotic | Treatment of neurodegenerative discorders and promotion of liver regeneration |
| CSA-FasL | Rat extracellular portion of FasL chimeric protein with core streptavidin | + | Apoptosis | Tolerance to allografts, xenografts, bone marrow transplantation, treatment of autoimmune diseases, allergies, asthma, septic shock, and other immune-induced diseases, and lymphocyte-dependent disorders, including tumors, and promotion of liver regeneration |
| CSA-hFasL | Human extracellular portion of Fas chimeric protein with core streptavidin | + | Apoptosis | Prevention of early reocclusion after coronary bypass surgery and angioplasty |
| CSA-TNFα | Human extracellular portion of TNF chimeric protein with core streptavidin | TNFα cDNA clone d | Apoptosis | |
| CSA-TWEAK | Human extracellular portion of TWEAK chimeric protein with core streptavidin | − | Apoptosis | |
| CSA-TRAIL | Human extracellular portion of TRAIL chimeric protein with core streptavidin | − | Apoptosis | |

The dosage necessary to induce apoptosis is dependent on the affinity and specificity of the apoptotic agent. Ten to 100 molecules of the preferred embodiment per cell, CSA/FasL, is sufficient for the apoptotic effect, while as much as 1,000 to 10,000 molecules of less active constructs may be necessary. The choice of apoptotic agent will depend on the activity desired.

A preferred production cell for the production of chimeric proteins encoded by the DNA constructs is the *Drosophila* system that is commercially available. However, those skilled in the art of producing chimeric proteins will recognize that many other expression systems and vectors are suitable for production of the chimeric proteins of this invention. Included in these other systems are *Escherichia coli*, yeast and mammalian cell cultures.

The experimental procedures described herein are representative of compositions and methods to regulate the immune system. These examples were designed to induce tolerance to autoantigens in the case of autoimmunity, allergies, and asthma and foreign antigens in case of allo and xenografts by application of the preferred embodiment to eliminate pathogenic immune cells expressing counter-death receptors. Furthermore, soluble forms of death ligands as monomers with none or minimal apoptotic activity will be used to interfere with apoptosis in neurodegenerative disorders and to promote liver regeneration. The most preferred embodiments are chimeric proteins, CSA-FasL, CSA-TNFα, CSA-TRAIL, and CSA-TWEAK produced by fusion of DNA coding for core streptavidin protein with that DNA coding for the mentioned death ligands and expressing the chimeric protein in a suitable production cell. These molecules are then purified and used either as purified proteins or used to decorate cells or organs to induce apoptosis in immune cells expressing the relevant death receptor. For example, cells of interest are first biotinylated ex vivo or in vivo and then CSA-death ligands are administered in order to attach the molecules to the cell surface for apoptosis of target lymphocytes, resulting in, for example, induction of antigen-specific tolerance for the prevention of autoimmunity and foreign graft rejection. Alternatively, purified chimeric proteins may be applied ex vivo or in vivo, leading to permanent elimination of antigen-specific pathogenic lymphocytes and the amelioration of the diseased condition. Soluble form of FasL and other death ligands consisting of extracellular domains will be used as purified protein with antiapoptotic function to prevent apoptosis in neurons for the treatment of neurodegenerative disorders in which unregulated apoptosis is the pathogenic mechanism. This molecule with the chimeric ones will also be used for liver regeneration. All these proteins can also be used to prevent septic shock, allergies, asthma, and food poisoning where activated lymphocytes play a major role.

EXAMPLE 1

Figure 2:
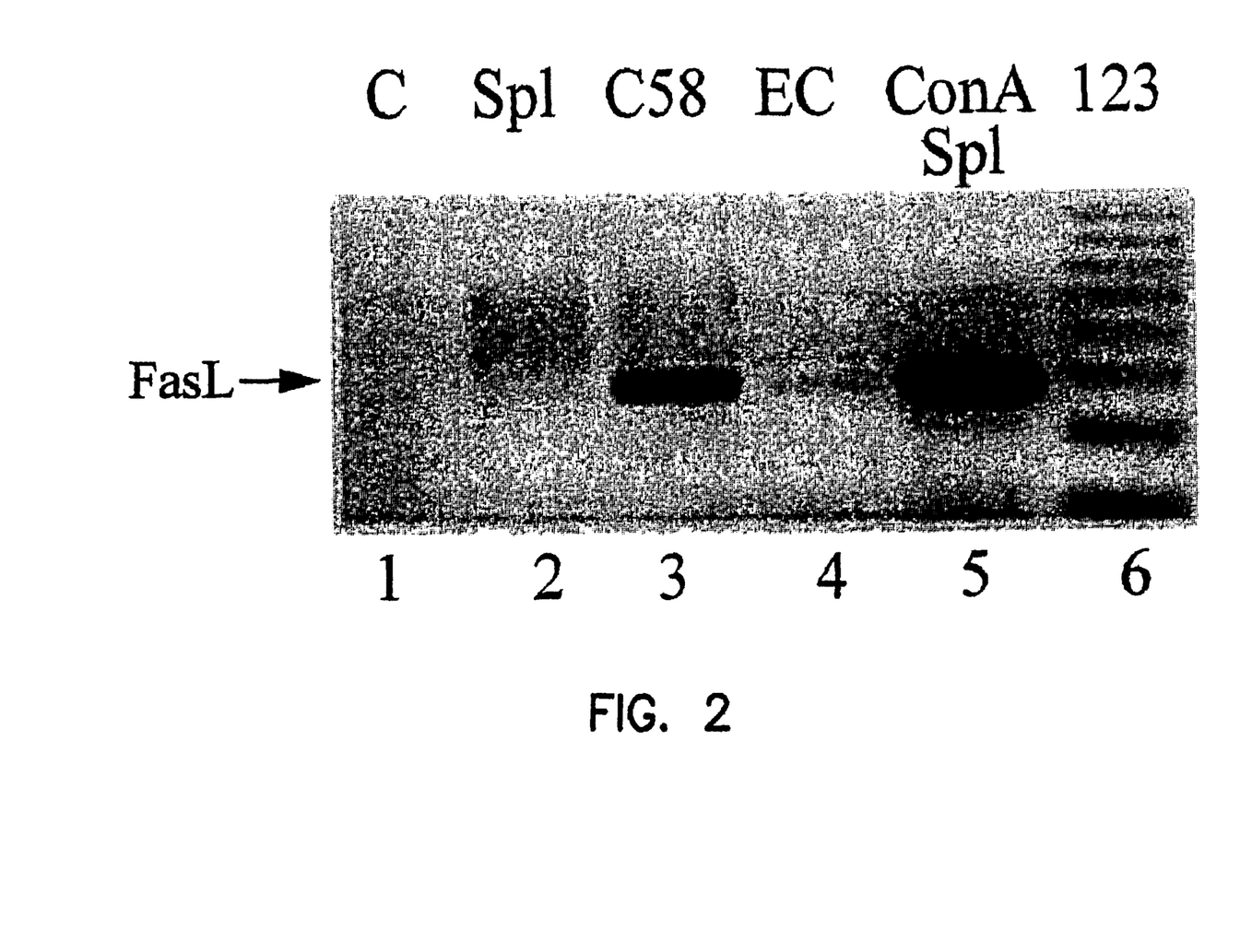
FIG. 2 shows the expression of Fas/FasL in activated splenocytes.

Cloning of Wild Type and Generation of a Membrane-Bound Form Of FasL, Expression in Mammalian Cells, and Test of Apoptotic Function A complete FasL cDNA was cloned from ConA-activated rat T cells or human peripheral blood cells using primers specific for the very 5'- and 3'-untranslated regions of the FasL mRNA in RT-PCR. The amplification product was then cloned into the TA cloning vector and several functional cDNA clones were determined by sequence analysis. A functional cDNA clone was then subcloned into the pcDNA3 eukaryotic expression vector (pcDNA3) and the recombinant clones containing cDNA in both the sense and the antisense orientations were determined by restriction site analysis. FIG. 2 shows the expression of FasL in different cell types as shown by gel electrophoresis. Total RNA was isolated from naive splenocytes (column 2); C58 cells (column 3), endothelial cells (column 4) and ConA-activated splenocytes (column 4). A PCR template (column 1) is shown as a negative control.

Although FasL is synthesized as a type II membranous protein, it is also secreted into the milieu as a soluble protein. The soluble form is generated from the membranous molecule by matrix metalloproteinases within minutes after its expression on the cell surface. FasL is also synthesized and stored as a membranous protein in microvesicles that are excreted into the milieu in selected cell types in response to various stimuli. These three different forms of FasL—membranous, soluble, and vesicular—may differ in their function with respect to apoptosis and immune regulation. Apoptosis is primarily mediated by vesicular and membranous forms of FasL whereas the soluble form is ineffective in mediating apoptosis and indeed serves as an antiapoptotic factor by competing with the membranous form for Fas. Furthermore, soluble FasL serves as a chemotactic factor for neutrophils whereas membranous and vesicular FasLs lack this function. Soluble FasL may, therefore, contribute to graft rejection by I) serving as an antiapoptotic molecule to prevent apoptosis of graft-reactive T cells, and ii) serving as a chemotactic factor for neutrophil infiltration into the graft. It is, therefore, important to separate the antiapoptotic and chemotactic functions of FasL from its apoptotic function for the use of FasL as a tolerogenic molecule.

Figure 3:
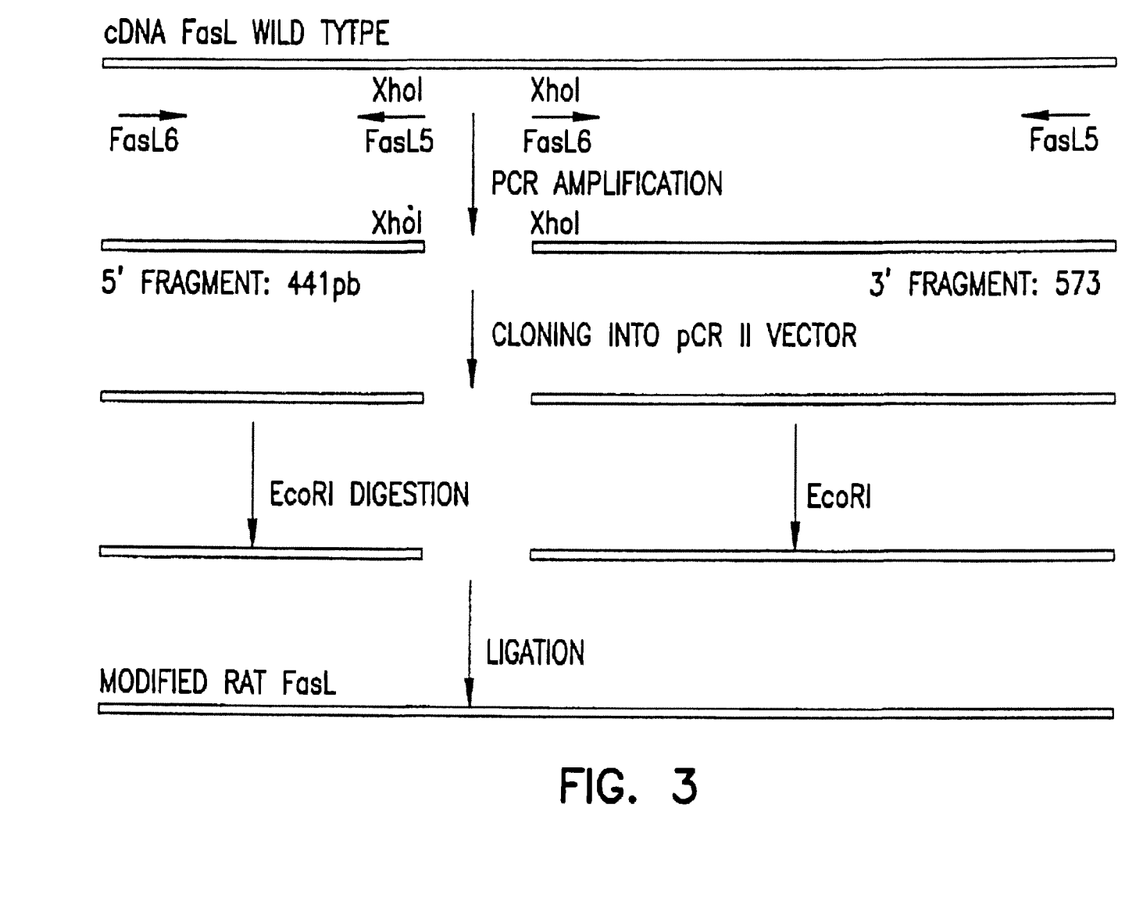
FIG. 3 shows the schematic diagram of modification of FasL to generate a stable cell surface protein.

We generated a rat FasL that is stably expressed on the cell surface by eliminating the putative metalloproteinase site. Oligonucleotide primers specific for FasL were designed by PCR to delete nucleotides encoding 12 amino acids residues thought to be metalloproteinase site (FIG. 3). DNA clones for the modified (mFasL) and wild type (wtFasL) were then transfected into PVG.IU rat endothelial cells and monkey Cos1 cells for expression. Stable transfectants were selected using G418 and analyzed for the expression of FasL molecules using RT-PCR and flow cytometry. RT-PCR analysis revealed high levels of expression of FasL in transfected cells but not in untransfected cells. Cos cells were transiently transfected with wtFasL and mFasL. Total RNA was prepared three days after transfection and used for RT-PCR with FasL-specific primers.

The PCR products were digested with XhoI enzyme. Most importantly, restriction digest of the PCR product with XhoI enzyme that was engineered into the cDNA for the modified form resulted in two bands in cells transfected with the mFasL but not wtFasL, confirming the modification. The expression of FasL at the protein level was confirmed using PE-labeled FasL mAb MFL4 in flow cytometry.

Figure 4:
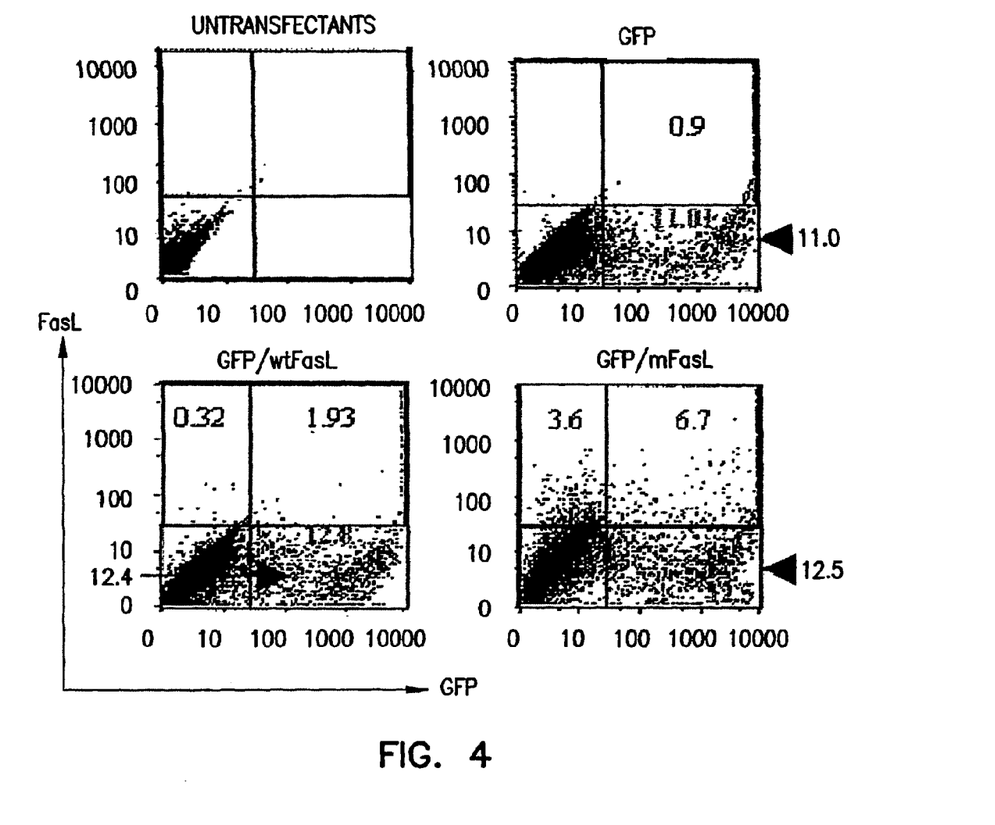
FIG. 4 shows the cell surface expression of FasL in Cos1 cells.

We obtained higher levels of expression of the modified FasL on the surface of transfected COS and endothelial cells as compared with wild type FasL (FIG. 4 is representative of four independent experiments). COS cells were transiently co-transfected with wtFasL, mFasL, and green fluorescence protein (GFP). Cells were analyzed for expression of FasL using PE-labeled MFL4 mAb and GFP. GFP was used as an internal control in order to access the efficiency of transfection.

Figure 5:
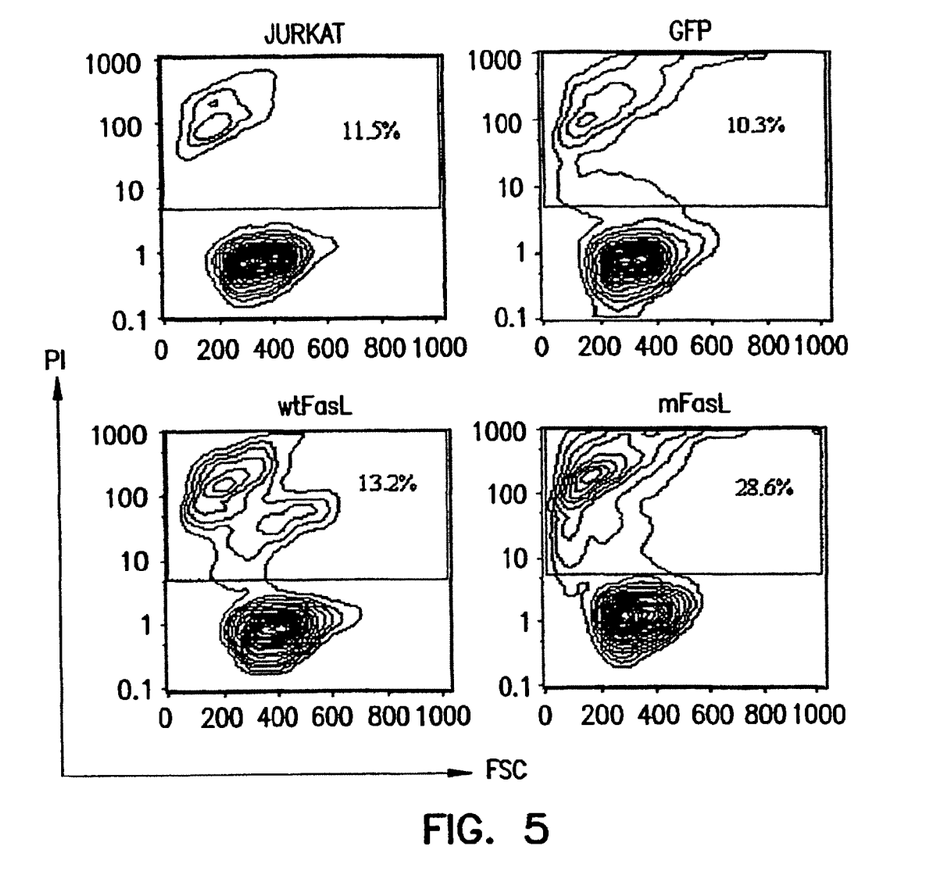
FIG. 5 shows efficient apoptosis of a human T cells line by Cos1 cells expressing the mFasL.

Transfectants expressing mFasL were much more effective in inducing apoptosis in apoptosis-sensitive human Jurkat cells as compared with transfectants expressing wtFasL (FIG. 5). COS cells were transiently transfected with wtFasL and mFasL. Three days after transfection, transfectants were co-incubated with Jurkat cells overnight and apoptosis was determined using PI in flow cytometry. Untransfected (Jurkat) and green fluorescence protein (GFP) transfected cells served as negative controls. The percentage of dead cells is shown in the upper quadrants of the histograms. The data is representative of a minimum of four independent experiments. Specific expression increased from 3.2% to 15.4%, while specific apoptosis increased from 6.5% to 23.8%.

EXAMPLE 2

Figure 6:
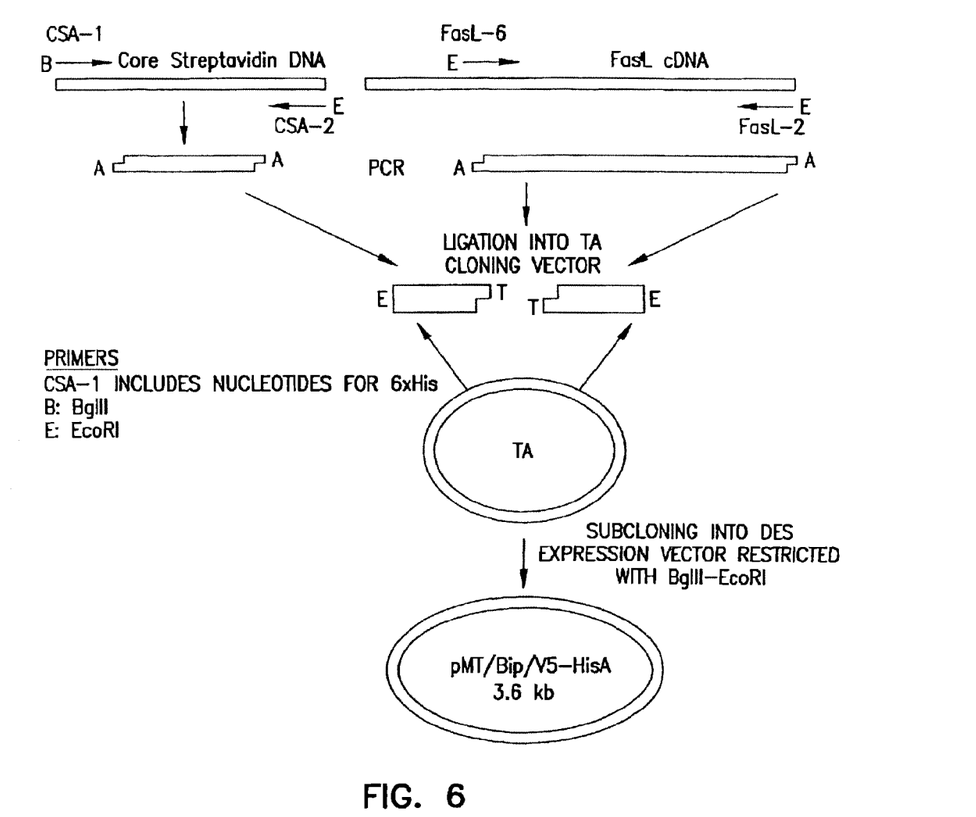
FIG. 6 shows the construction of CSA-FasL construct.

Construction of a Chimeric Core Streptavidin and FasL (CSA-FasL), its Expression, and Function We next generated a construct encoding core streptavidin (CSA) fused in frame with the extracellular domain of FasL lacking the putative metalloproteinase site using the scheme outlined in FIG. 6. Genomic DNA was isolated from *Streptomyces avidinii* (ATCC Cat.#27419) and 0.2 g of this DNA was used as template for amplification using primers specific for 5'-end (CSA-I) and 3'-end (CSA-2) of core streptavidin in PCR. The 5'-primer included sequences for BgIII and 6 His residues to allow cloning in frame with the *Drosophila* secretion signal (BiP) for expression as a secreted protein and purification using NI-affinity columns. The PCR product was cloned into the TA cloning vector and several positive clones were identified first screening by PCR and then digestion with restriction enzymes. We next subcloned the extracellular domain of the FasL without the metalloproteinase site using the wild type FasL cDNA clone as a template and a sense primer to the 5'-end of the extracellular region, FasL6 containing an EcoR1 site, and an antisense primer to the 3'-end untranslated region of FasL, FasL2 containing an EcoRI site in frame with CSA, in PCR. The PCR product was then cloned into the TA cloning vector and several positive clones were identified by restriction digestion. Both the core streptavidin and extracellular FasL clones were then sequenced and DNA inserts with accurate sequences were digested out of the TA cloning vector with BgIII-EcoRI for CSA and EcoRI for extracellular FasL. These DNA inserts were then subcloned into the BgIII-EcoRI-cut pMT/BiP/V5-His vector for expression in using the DES system (Invitrogen).

Figure 7A:
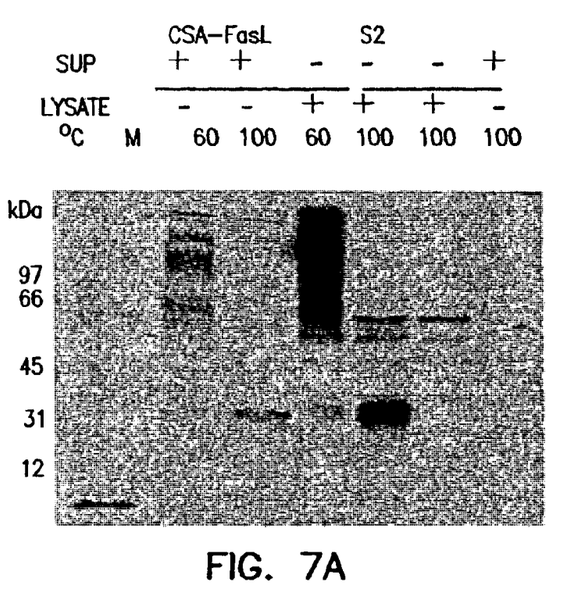
FIG. 7 shows the expression of soluble and CSA-FasL by Western blot.
Figure 7B:
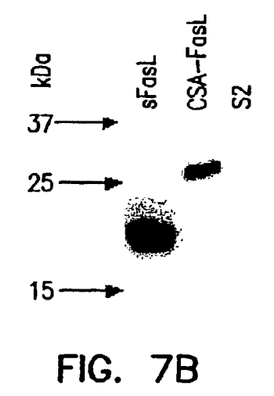
Figure 9:
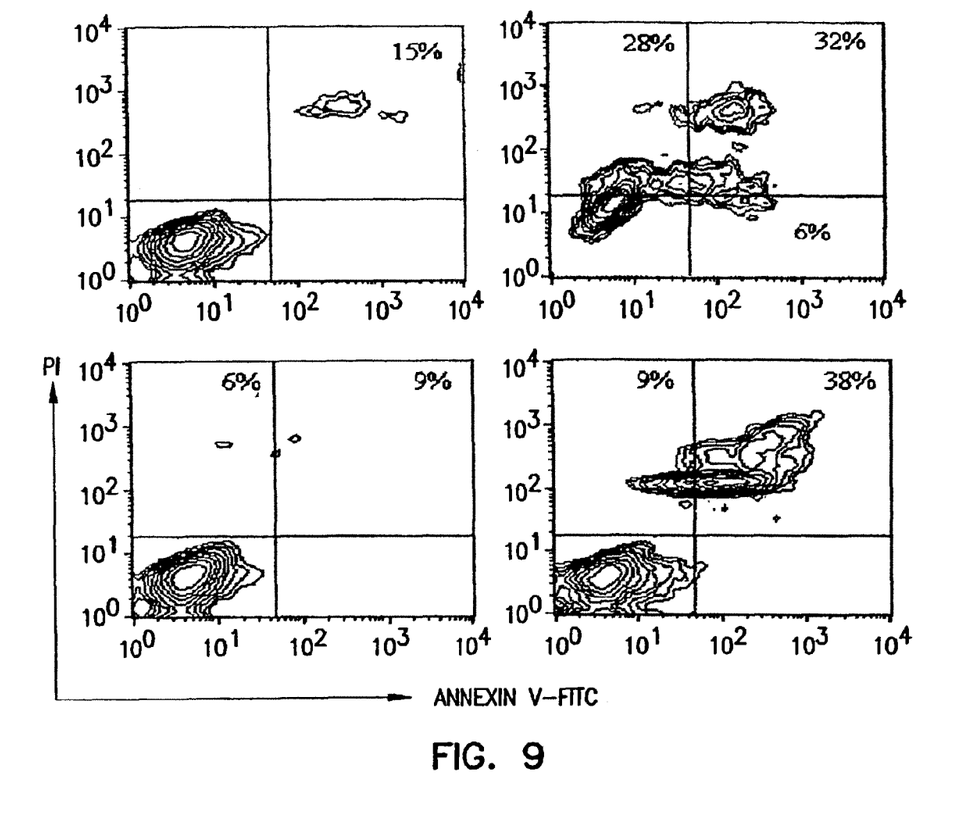
FIG. 9 shows apoptosis of Jurkat cells by cell-surface or agarose beads-bound CSA-FasL.
Figure 10:
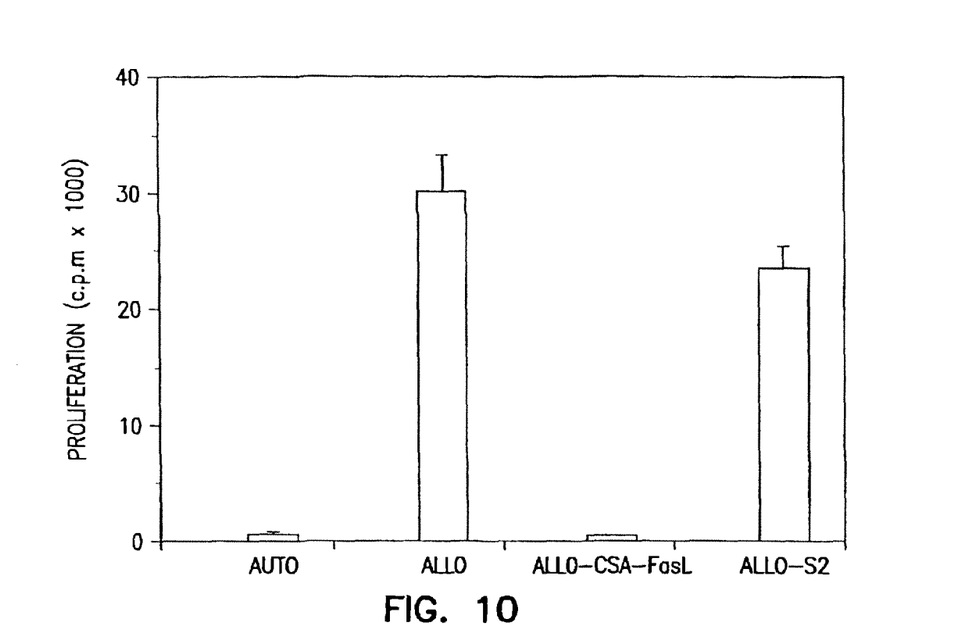
FIG. 10 shows the blockade of alloreactive responses by cells decorated with CSA-FasL.

S2 cells were transfected transiently with the recombinant CSA/FasL plasmid using calcium phosphate transfection according to the manufacture's instructions (Invitrogen). S2 cells were pulsed with copper sulfate 24 hr after transfection to activate the metallothionein promoter for expression of the chimeric CSA-FasL protein. Culture medium was then collected after a 24-hr induction period and analyzed by ELISA and Western blot. It was seen that mAb MFL4 against FasL (PharMingen, San Diego, Calif.) detects a band of ~35 kDa corresponding to the expected molecular weight of the chimeric protein in Western blots performed under stringent denaturing conditions. The identity of the chimeric protein was either confirmed using polyclonal antibodies against streptavidin (Zymed Laboratories, San Francisco, Calif.), which detected the same band (data not shown). CSA forms tetramers that are stable in 1% SDS and 10% mercaptoethanol solution at temperatures under 60° C. Culture supernatants were, therefore, heated at 60 and 100° C. before mining on SDS-PAGE to test if the chimeric protein forms tetramers. As shown in FIG. 9, mAb MFL4 against FasL (PharMingen, San Diego, Calif.) detected bands of ~35 and >100 kDa at 60° C. and primarily a band of ~35 kDa at 100° C. These bands correspond to expected monomers and tetramers (FIG. 7). These bands were only detected in S2 cells transfected with CSA-FasL construct (lane FasL) but not cells transfected with a nonfunctional FasL (lane S2; one nucleotide insertion near to 5' end of the cDNA during the cloning process leads to a shift in the reading frame and lack of the protein expression).

The expression of CSA-FasL by S2 cells was further confirmed using biotin-coated microwell strip plates in ELISA. Briefly, biotinylated wells were incubated with culture supernatants for 45 min at room temperature, washed extensively, and then incubated with the working concentrations of primary antibodies against streptavidin or FasL (MFL4) for 45 min at room temperature. Wells were then washed extensively and incubated with alkaline phosphatase conjugated secondary antibodies at room temperature for 45 min. Plates were then washed extensively and incubated with alkaline phosphatase substrate. Data was analyzed using an ELISA reader (Victor, Wallac, Gaithersburg, Md.). Both antibodies detected high levels of CSA-FasL in S2 cells expressing CSA-FasL (FasL) but not negative controls (S2). Most importantly, we quantified the amount of CSA-FasL expressed by the transfectants using known amounts of pure streptavidin protein as standard (Pierce). Transfectants expressed 50-100 ng of chimeric protein/ml of culture medium. Taken together, these data clearly demonstrate that we have succeeded to generate a functional chimeric CSA-FasL construct and express it in S2 cells, and developed experimental methods for detection and quantification of the chimeric protein.

We also generated a construct consisting of the human extracellular portion of FasL with CSA, extracellular portion of rat FasL (FIG. 7b), and cloned a cDNA for human extracellular portion of TNF- to generate a chimeric CSA-TNFα.

EXAMPLE 3

Figure 8A:
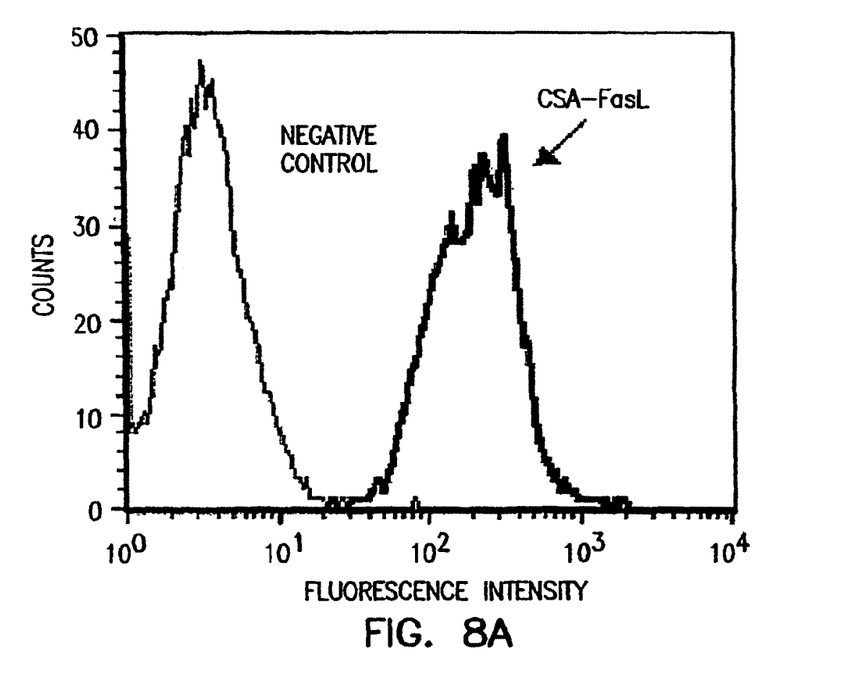
FIG. 8 shows binding of CSA-FasL to the surface of splenocytes.
Figure 8B:
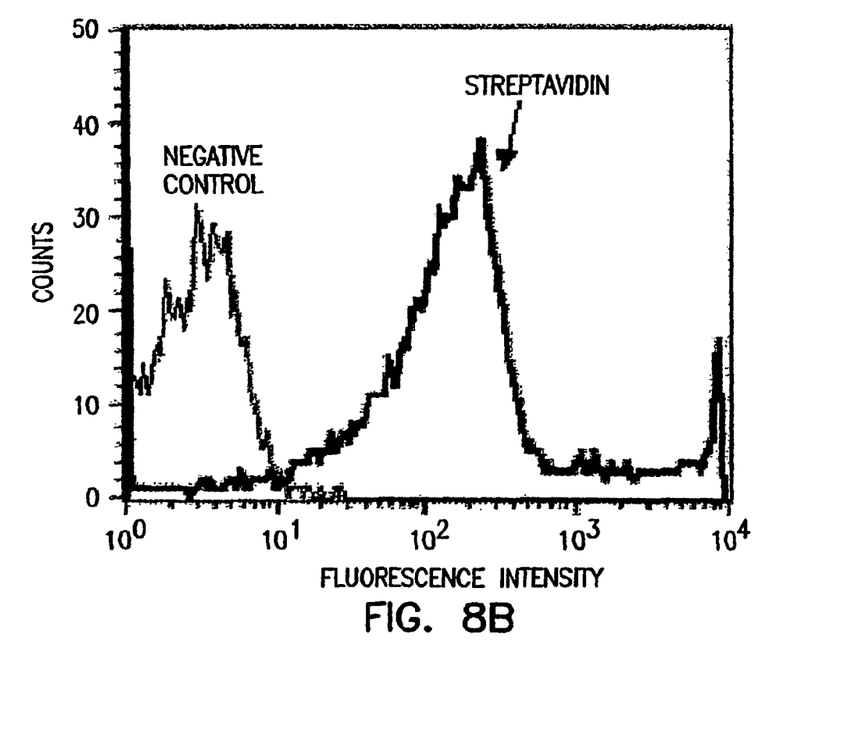

Expression of Chimeric CSA-FasL Molecule on the Surface of Splenocytes for Analysis of its Function in Apoptosis To test whether chimeric CSA-FasL can be attached to the cell surface under physiological conditions, $2.5 \times 10^7$ PVG.R8 splenocytes were conjugated with EZ-Link Sulfo-NHS-LC-Biotin (15 μM) in 1 ml of PBS at room temperature for 30 min according to the manufacturer's instructions (Pierce). After several washes in PBS, pH 8.0, $1 \times 10^6$ cells were incubated in 0.3-1 ml culture supernatants containing 50-100 ng CSA-FasL or supernatants from S2 cells transfected with a nonfunctional FasL construct for 45 min on ice. Cells were washed extensively and used for FasL staining or apoptosis assays. Staining was performed on $1 \times 10^6$ cells using APC-streptavidin or a monoclonal antibody (MFL4) conjugated with PE in flow cytometry. All the cells expressed CSAFasL (FIG. 8a) and streptavidin (FIG. 8b). Supernatant from S2 control was negative for FasL staining. Similarly, splenocytes without biotinylation did not stain with APC-streptavidin, demonstrating specificity.

We next tested decorated splenocytes for apoptosis. Effector splenocytes were washed with PBS three times and $1 \times 10^6$ cells were co-incubated with $1 \times 10^6$ Jurkat cells in RPMI culture medium overnight for apoptotic activity. Apoptosis in Jurkat cells was determined by using propidium iodide (a marker for dead cells), Annexin V-FITC (a marker for early apoptotic events), and human anti-CD3-APC mAb (clone UCHTI; PharMingen) to gate specifically on Jurkat cells using flow cytometry. Significant apoptosis was detected in the culture where Jurkat cells were co-incubated with splenocytes-FasL as compared with control cultures incubated with S2 supernatant without FasL (38% versus 9%) (FIG. 9).

In some clinical situations, it may be advisable to purge the activated T cells of the patient without inducing a permanent effect. Many techniques are known for removal of blood continuously from the body, subjecting it to treatment outside the body with subsequent return. A patient suffering from an autoimmune disease will especially benefit from leukophoresis, in which the white cells are continuously collected, followed by treatment with one of the recombinant proteins of this invention. Those activated lymphocytes killed via apoptosis will be removed and the leukocytes returned to the patient. In this manner, the pathogenic immune cells are removed from the body of the patient without major side effects of the treatment. We, therefore, conjugated the chimeric CSA-FasL molecule to biotin-agarose beads (ImmunnPure® immobilized immunobiotin; Pierce) and tested the function for apoptosis of Jurkat cells. As shown in FIG. 12, CSA-FasL induced significant apoptosis (38%) in Jurkat cells as compared with the beads without FasL (15%). Treatment of mouse A20 cell line under similar experimental conditions results in >90% death as this cell line is more sensitive to apoptosis.

EXAMPLE 4

FasL Expressing Cells Completely Block Alloreactive Responses When Used as Targets We next tested cells decorated with CSA-FasL for the induction of apoptosis in responding lymphocytes in mixed lymphocyte culture (MLR), a test frequently used in clinical situations to test the antigenic compatibility between the donor and graft recipients and to test for tolerance. ACI splenocytes were conjugated with EZ-Link Sulfo-NHS-LC-Biotin (5 μM) in 1 ml of PBS at room temperature for 30 rain according to the manufacturer's instructions (Pierce). After several washes in PBS, pH 8.0, $1 \times 10^6$ cells were incubated in 0.3-1 ml culture supernatants containing 50-100 ng CSA-FasL or supernatants from S2 cells transfected with a non-functional FasL construct for 20 min on ice. Cells were washed extensively, irradiated (2000 cGy) and used as targets for PVG.IU lymph node cells at 1:1 ratio ($1 \times 10^5$ cell/well). Cultures were harvested at various days after pulsing with 1 M/well $^3$H-thymidine for 18 hours and assessed for proliferation. As shown in FIG. 13, CSA-FasL-decorated cells completely blocked the response. This blockage was CSA-FasL specific as biotinylated cells generated a normal response.

EXAMPLE 5

Figure 11:
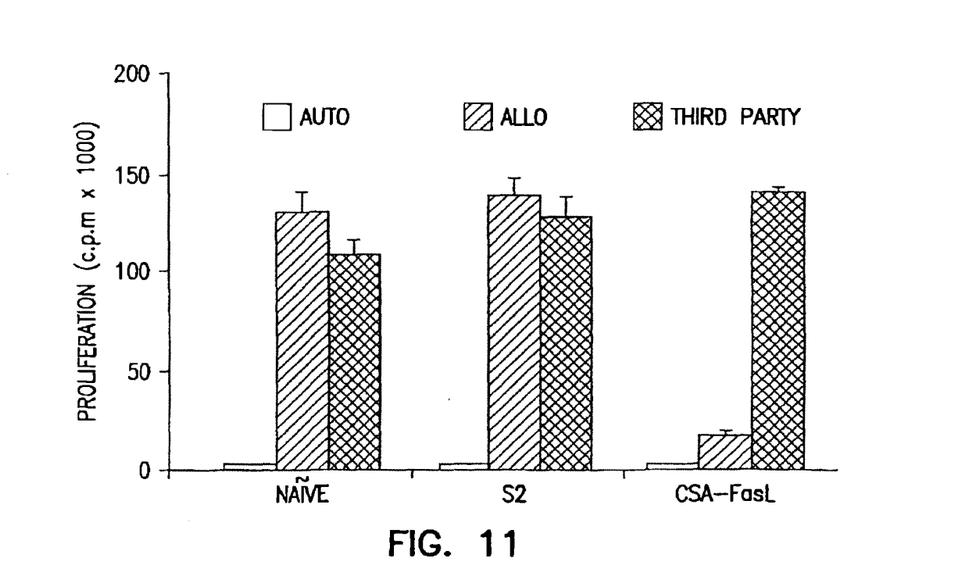
FIG. 11 shows the blockade of alloreactive responses in vivo by cells decorated with CSA-FasL.

FasL Expressing Cells Completely Block Alloreactive Responses When Used as Targets The potent effect of CSA-FasL-splenocytes to block in vitro alloreactive responses led us to test the role of these cells in blocking alloreactive responses in vivo. PVG.IU rats were immunized i.v. or i.p. with irradiated (2000 cGy) 1×10⁷ ACI cells decorated with FasL or control S2 supernatant. Mesenteric lymph nodes were harvested 7 days after injection and used as responders to ACI cells in a standard mixed lymphocyte assay. There was a complete absence of response to donor antigens (FIG. 11). This in vivo immune nonresponsiveness was donor specific as the response to third party antigens (LEW) was intact. This effect was FasL-specific as animals receiving ACI cells treated with control S2 supernatant generated a normal response to donor as well as third party antigens as compared with the response of naive animals.

EXAMPLE 6

FasL Expressing Cells Prevent Rejection of Islet Allografts

We next tested whether the potent immunosuppressive effect of FasL observed in vitro and in vivo is sufficient for prevention of islet allograft rejection. Diabetes was induced in BALB/c recipients by i.p. injection of streptozocin (260 mg/kg). Animals demonstrating blood glucose levels >450 mg/dl for at least 3 consecutive days were used as recipients of minor+major histocompatibility antigens-disparate BI0 islets. Islets were harvested from C57BL/10 mice and isolated on a Ficoll gradient according to a standard protocol. Splenocytes were harvested from B10 mice, biotinylated (15 µM), decorated with FasL (50-100 ng/10⁶ cells) or control S2 supernatant, and irradiated (2000 rads). One million of splenocytes were co-transplanted with ~400 islet cells under the kidney capsule of diabetic BALB/c mice. Survival of islets was assessed by monitoring blood glucose levels starting 3 days after transplantation. FasL-decorated splenocytes prevented the rejection of ~70% of allogeneic islets (MST>56 day;). In marked contrast, all the recipients co-transplanted with control S2-treated splenocytes and allogeneic islets rejected allografts in a normal tempo (~11 days). Two of the FasL-treated recipients rejected islets in ~15 days (blood glucose level >250 mg/dl for 3 consecutive days) whereas six recipients currently maintain blood glucose levels of less than 250 mg/dl on 56 days after transplantation. The results presented in this section support our hypothesis that recognition of alloantigens in the presence of FasL leads to functional elimination of alloreactive T cells and prolonged allograft survival. Table II is a summary of these results.

TABLE II

Survival of C57BL/10 allogeneic islets in Balb/c mice

| Group | Number | Transplantation | Survival time, days |
|---|---|---|---|
| A | 5 | Islet | 7, 8, 9, 10, 10 |
| B | 5 | Islet + splenocytes-S2 | 3, 3, 8, 10, 10 |
| C | 10 | Islet + splenocytes-FasL | 15, 17, 21, 38, >56, >56, >56, >56, >56, >56 |

EXAMPLE 7

Other Useful Constructs

The data presented demonstrate:
1. Successful cloning and generation of most of the proposed constructs in Table 1;
2. Expression of wtFasL, modified FasL, soluble FasL, and CSA-FasL in mammalian and insect cell lines;
3. Purification of the proteins;
4. Induction of apoptosis in cell lines using FasL;
5. Prevention of alloreactive responses in vitro and in vivo using CSA-FasL as an immune modulator;
6. Most importantly, splenocytes expressing CSA-FasL prevented the rejection of islet allograft; and
7. Chimeric protein can be produced with human FasL; the cDNA has been cloned and the protein is under construction.

These findings provide proof of concept for the hypothesis that modified death ligands forming tetramers can be efficiently used for immune modulation to treat autoimmunity and prevent foreign graft rejection. We predict successful application of this approach to the treatment of disorders listed in Table 1 and alluded to in the body of this application.

While the examples described herein provide the biotin/streptavidin pair for direction of the constructs to the targeted cells, it is well known that other such pairs exist. Avidin can be substituted for streptavidin. The binding regions of antibodies are specific to antigens. It is within the skill of those in the art to produce an antibody directed against a cell surface protein such as a tumor antigen protein. Recombinant binding regions (Fabs) or isolated variable regions (Hv plus Lv) of such antibodies are readily made. Following the teachings of this invention, one skilled biotechnology can, without undue experimentation, construct a chimeric protein comprising FasL or mFasL and the binding regions of antibodies to a cell surface protein unique to the targeted cell. Such a chimeric protein can be administered to cause apoptosis in the tumore, thereby reducing tumor load. Many other such modifications or variations of this invention may readily be made without departing from the spirit and scope of this invention. Therefore, all such modifications or variations are considered to be within the scope of the appended claims.

What is claimed is:

1. A method for inducing apoptosis in an activated lymphocyte, comprising exposing said activated lymphocyte to an effective amount of a chimeric protein comprising:
    (i) an apoptosis-inducing moiety selected from the group consisting of Fas-ligand (FasL) and the extracellular portion thereof, tumor necrosis factor α(TNFα) and the extracellular portion thereof, TNF-like weak inducer of apoptosis (TWEAK) and the extracellular portion thereof, and TNF-related apoptosis inducing ligand (TRAIL) and the extracellular portion thereof; and
    (ii) a member of a binding pair selected from the group consisting of avidin and streptavidin;
    wherein the chimeric protein is attached ex vivo to a biotinylated solid matrix or a biotinylated effector cell and wherein said exposing is effected ex vivo or in vivo.

2. The method of claim 1, wherein the activated lymphocyte cell membrane comprises biotin.

3. The method of claim 1, wherein the apoptosis-inducing moiety is selected from the group consisting of wild type FasL (wtFasL), the extracellular portion of FasL and the soluble extracellular portion of rat FasL (rsFasL).

4. The method of claim 1, wherein the chimeric protein forms tetramers.

5. The method of claim 1, wherein the member of a binding pair is streptavidin.

6. The method of claim 5, wherein the streptavidin is core streptavidin.

7. The method of claim 1, wherein the chimeric protein is attached to a biotinylated solid matrix.

8. The method of claim 7, wherein the biotinylated solid matrix is a biotin-agarose bead.

9. The method of claim 1, wherein the chimeric protein is attached to a biotinylated effector cell.

10. The method of claim 9, wherein the effector cell is selected from the group consisting of splenocytes, islet cells, bone marrow cells, and T-cells.

11. The method of claim 10, wherein the effector cell is part of a tissue or organ.

12. The method of claim 1, wherein said exposing is effected in vivo.

13. The method of claim 1, wherein said exposing is effected ex vivo.

14. A method for inducing apoptosis in an activated lymphocyte, comprising exposing said activated lymphocyte to an effective amount of an effector cell, wherein the cell membrane of said effector cell comprises (A) biotin bound to (B) a chimeric protein comprising (i) an apoptosis-inducing moiety selected from the group consisting of Fas-ligand (FasL) and the extracellular portion thereof, tumor necrosis factor α(TNFα) and the extracellular portion thereof, TNF-like weak inducer of apoptosis (TWEAK) and the extracellular portion thereof, and TNF-related apoptosis inducing ligand (TRAIL) and the extracellular portion thereof; and (ii) a member of a binding pair selected from the group consisting of avidin and streptavidin,
wherein said chimeric protein is attached to said effector cell ex vivo, and
wherein said exposing is effected ex vivo or in vivo.

15. The method of claim 14, wherein the apoptosis-inducing moiety is selected from the group consisting of wild type FasL (wtFasL), the extracellular portion of FasL and the soluble extracellular portion of rat FasL (rsFasL).

16. A method of inducing immune modulation in a mammal in need thereof by inducing apoptosis in an activated lymphocyte comprising administering to the mammal an effective amount of an effector cell, wherein the cell membrane of said effector cell comprises (A) biotin bound to (B) a chimeric protein comprising (i) an apoptosis-inducing moiety selected from the group consisting of Fas-ligand (FasL) and the extracellular portion thereof, tumor necrosis factor α(TNFα) and the extracellular portion thereof, TNF-like weak inducer of apoptosis (TWEAK) and the extracellular portion thereof, and TNF-related apoptosis inducing ligand (TRAIL) and the extracellular portion thereof; and (ii) a member of a binding pair selected from the group consisting of avidin and streptavidin,
wherein said chimeric protein is attached to said effector cell ex vivo, and wherein said exposing is effected ex vivo or in vivo.

17. The method of claim 16, wherein the apoptosis-inducing moiety is selected from the group consisting of wild type FasL (wtFasL), the extracellular portion of FasL and the soluble extracellular portion of rat FasL (rsFasL).

18. The method of claim 16, wherein the mammal has a condition selected from the group consisting of asthma, allergy, food poisoning, autoimmunity and transplantation of allogeneic or xenogeneic tissue.

19. The method of claim 18, wherein the autoimmune condition is selected from the group consisting of diabetes, multiple sclerosis, lupus erythematosis, sarcoidosis and rheumatoid arthritis.

20. A method of inducing immune tolerance in a mammal comprising:
(a) removing lymphocytes from said mammal;
(b) exposing ex vivo said lymphocytes to an effective amount of a chimeric protein comprising (i) an apoptosis-inducing moiety selected from the group consisting of Fas-ligand (FasL) and the extracellular portion thereof, tumor necrosis factor α(TNFα) and the extracellular portion thereof, TNF-like weak inducer of apoptosis (TWEAK) and the extracellular portion thereof, and TNF-related apoptosis inducing ligand (TRAIL) and the extracellular portion thereof; and (ii) a member of a binding pair selected from the group consisting of avidin and streptavidin, wherein said chimeric protein is bound to a biotinylated matrix; and
(c) returning said lymphocytes to said mammal.

21. The method of claim 20, wherein the apoptosis-inducing moiety is selected from the group consisting of wild type FasL (wtFasL), the extracellular portion of FasL and the soluble extracellular portion of rat FasL (rsFasL).

22. A method of inducing immune modulation in a mammal in need thereof by inducing apoptosis in an activated lymphocyte comprising administering to the mammal an effective amount of a chimeric protein comprising (i) an apoptosis-inducing moiety selected from the group consisting of Fas-ligand (FasL) and the extracellular portion thereof, tumor necrosis factor α(TNFα) and the extracellular portion thereof, TNF-like weak inducer of apoptosis (TWEAK) and the extracellular portion thereof, and TNF-related apoptosis inducing ligand (TRAIL) and the extracellular portion thereof; and (ii) a member of a binding pair selected from the group consisting of avidin and streptavidin;
wherein the chimeric protein is attached to a biotinylated solid matrix or a biotinylated effector cell ex vivo, and wherein said exposing is effected ex viva or in viva.

23. The method of claim 22, wherein the apoptosis-inducing moiety is selected from the group consisting of wild type FasL (wtFasL), the extracellular portion of FasL and the soluble extracellular portion of rat FasL (rsFasL).

* * * * *